United States Patent [19]
Helmreich et al.

[11] Patent Number: 6,117,127
[45] Date of Patent: Sep. 12, 2000

[54] MEDICAL SYSTEM WORK STATION

[75] Inventors: Gerhard Helmreich; Bernd Malter, both of Effeltrich; Manfred Rattner, Grossenseebach; Thomas Reichert, Erlangen, all of Germany

[73] Assignee: Siemens Aktiengesellschaft, Munich, Germany

[21] Appl. No.: 09/072,175

[22] Filed: May 5, 1998

[30] Foreign Application Priority Data

| May 7, 1997 | [DE] | Germany | 197 19 369 |
| Mar. 31, 1998 | [DE] | Germany | 198 14 367 |

[51] Int. Cl.⁷ ................................................ A61B 17/00
[52] U.S. Cl. .................................................. 606/1; 606/10
[58] Field of Search .................................. 606/1, 4, 5, 6, 606/10, 11, 12, 14, 15, 16

[56] References Cited

U.S. PATENT DOCUMENTS

| 4,069,823 | 1/1978 | Isakov et al. | 606/19 |
| 5,098,426 | 3/1992 | Sklar et al. | 606/5 |
| 5,150,704 | 9/1992 | Tatebayashi et al. | 606/19 |
| 5,464,013 | 11/1995 | Lemelson | 606/10 |
| 5,531,740 | 7/1996 | Black | 606/11 |
| 5,662,644 | 9/1997 | Swor | 606/10 |
| 5,788,688 | 8/1998 | Bauer et al. | 606/10 |

FOREIGN PATENT DOCUMENTS 92 18 373 U  10/1994  Germany.

Primary Examiner—Linda C. M. Dvorak
Assistant Examiner—Roy Gibson
Attorney, Agent, or Firm—Hill & Simpson

[57] ABSTRACT

A medical system work station for open or minimally invasive surgery, has a holder tray and at least one terminal unit for handheld instruments of one or more medical devices, at least one equipment center, spatially separated from the terminal unit, for accepting non-manipulated components of the medical devices, and at least one connection unit that connects the terminal unit and the equipment center with one another.

11 Claims, 3 Drawing Sheets

MEDICAL SYSTEM WORK STATION

BACKGROUND OF THE INVENTION

1. Field of the Invention

The present invention is directed to an invasive surgery work station having manual (handheld) instruments of one or more medical devices, an equipment cabinet for housing non-manipulated components of the medical devices, and a connection unit that connects the instruments and the equipment cabinet with one another.

2. Description of the Prior Art

In open or minimally invasive surgery (collectively referred to herein as "invasive surgery"), medical devices with widely varying functions are used simultaneously in operations. The devices are generally constructed as independent units, and are arranged more or less systematically, relatively closely around a patient positioning table that accepts a patient. It is disadvantageous that the devices occupy a considerable space in the region around the patient positioning table, so that this space is not available to the operating team (consisting of physicians, auxiliary personnel and operational personnel for the equipment), so that the operating team's work often has to be carried out in very limited space.

Another disadvantage of the known work stations is that several operators are required just to operate the devices, which is economically disadvantageous.

A medical work station is known, for example, from German Utility Model 92 18 373 which has an equipment cabinet for holding non-manipulated components of one or more medical devices. The equipment cabinet of this known work station is placed immediately alongside the patient positioning table, so that the patient positioning table is not freely accessible. Moreover, there is no central location from which all of the handheld instruments can be readily accessible.

SUMMARY OF THE INVENTION

An object of the present invention is to provide a medical work station wherein all of the handheld instruments necessary for conducting a particular open or minimally invasive surgical procedure are readily available at a single common location (concentrated region), and good access is nevertheless provided to the space around the patient positioning table.

This object is achieved according to the invention in a medical system work station for open or minimally invasive surgery, having a holder tray and at least one terminal unit for handheld instruments of one or more medical devices, at least one equipment center, spatially separated from the terminal unit, for housing non-manipulated (stationary) components of the devices, and at least one connection unit, which connects the terminal unit and the equipment center with one another. The holder tray accepts all the handheld instruments required for a surgical intervention, so that they are centrally ready on a single unit to be picked up by or handed to the surgeon. The terminal unit is generally arranged not far from the holder tray, in order to keep the terminal lines between the handheld instruments and the terminal unit as short as possible. Since the non-manipulated device components are arranged in an equipment center that is spatially separated from the terminal unit, and are connected with the terminal unit via the connection unit, the space around a patient positioning table of the system work station is no longer blocked by individual devices, so that good access is provided to the patient positioning table. As used herein, the term "spatial separation" means that the equipment center is arranged at a distance of at least 1.5 meters from the patient positioning table, or from the terminal unit, and the equipment center can even be arranged outside the operating room. A further advantage of the invention is that all the devices can be centrally operated from the equipment center by a single person, resulting in a savings in operating personnel. This primarily has a positive economic effect.

As used herein, the term "handheld instruments" encompasses any type of article associated with any type of surgical, examination, or diagnostic apparatus of the type employed in an operating room environment. As used herein, therefore, the term "handheld instruments" is not necessarily limited to an article which performs primarily medical functions, but encompasses any type of article which is used to prepare for, conduct, assist in or augment an interventional medical procedure.

In an embodiment of the invention, the holder tray and the terminal unit are arranged on a presenting unit, which is preferably of movable (mobile) construction. In this way, the holder tray can be displaced (e.g. relative to a patient positioning table of the system work station) in common with the instruments of the medical devices and the terminal unit, which are connected with one another via the terminal lines of the instruments.

In a preferred embodiment of the invention the holder tray has at least one computer operating device that is connected, via the connection unit, with at least one control computer of the system work station. The medical devices are also connected with the control computer. The control computer is thereby preferably operated by menu-controlled software with menu selections being made by the computer operating device, which makes it possible to operate all devices connected to the control computer centrally from the control computer. In this way, the surgeon can also operate all the devices centrally from the holder tray via the operating device connected to the control computer, which can be, for example, a joystick, a foot switch or a receiving unit for voice control. A display connected to the control computer is provided, which is preferably a monitor arranged in the surgeon's field of view. Due to the fact that operating tasks are carried out personally by the surgeon, this embodiment of the invention makes it possible to save additional operating personnel, thereby further increasing the economy of the inventive system work station.

In a version of this embodiment of the invention, the medical devices, the operating device and the control computer are connected with one another via a communication bus. The communication bus represents a particularly advantageous technical connection of the individual devices, the operating device and the control computer with one another, since it is suited for digital signal transmission between the operating device, the control computer and the medical devices.

The equipment center can be provided with a number of receptacles for the respective medical devices. The receptacles are preferably of the same type, but can be partly of differing construction from one another, so that all medical devices required for an open or minimally invasive surgical intervention can be integrated into the equipment center. It is possible in some circumstances to house components of devices in one receptacle that are different, but whose terminals are substantially identical. A modular construction system of comparable devices thus can be both added to and removed from the equipment center. In this way, the system work station can be configured with different combinations of devices that can be adapted to the respective operating room environment. For the instruments of the devices in question, or the control units of the devices, corresponding terminals are provided on the terminal unit of the system work station. The devices in question include, for example high-frequency generators, suction and rinsing pumps, ultrasound equipment, insufflators, endoscopy cameras, cold light apparatuses, boring means, lasers, etc., or control units therefor.

In an embodiment of the invention the control computer is integrated into the equipment center. This embodiment of the invention is particularly advantageous because no further space is required in the operating room for the control computer. In addition, the otherwise necessary connection lines between the equipment center and the control computer, which would represent obstacles (danger of stumbling) in the operating room, are omitted.

The equipment center can be provided with a receptacle for at least one image memory. The provision of an image memory enables of stored image information to be called, e.g. during a surgical intervention, directly by the surgeon, so that the surgeon can compare newly recorded image information with already-recorded and stored image information, if this is required. The comparison of the image information can take place sequentially or by direct positioning opposite one another, e.g. in the form of a double image display on a bifurcated display screen.

In a preferred embodiment of the invention, the connection unit has connection lines in the form of electrical connection cables and/or light waveguides and/or compressed-air lines and/or gas lines, with the capability of electrical connecting cables, light waveguides, compressed-air lines or gas lines being added to or removed from the connection unit. In this way, the handheld instruments of the medical devices can be supplied with electrical energy, compressed air or gas for their particular operation. In addition, the transmission of image signals, light or the transmission of control signals can ensue via the electrical connecting cable or light waveguides. The multiplicity of connection lines made available, or the capability of expansion by additional connection lines, enables the use of a large variety of medical devices at the system work station.

According to a further embodiment of the invention, the connection unit is a ribbon conductor laid on the floor, or is a ceiling-mounted channeled tube, the ribbon conductor or the channeled tube accepting the electrical connection cable, the light waveguides, the compressed-air lines and the gas lines, which connect the terminal unit with the equipment center, and thus with the individual medical devices. In this way, the various connection lines do not present an obstacle in the operating room, since they are either laid flat on the floor, integrated into the ribbon conductor, and are easy to cross over, or are routed on the ceiling, integrated into the channeled tube, outside the area of movement of personnel.

DESCRIPTION OF THE PREFERRED EMBODIMENTS

Figure 1:
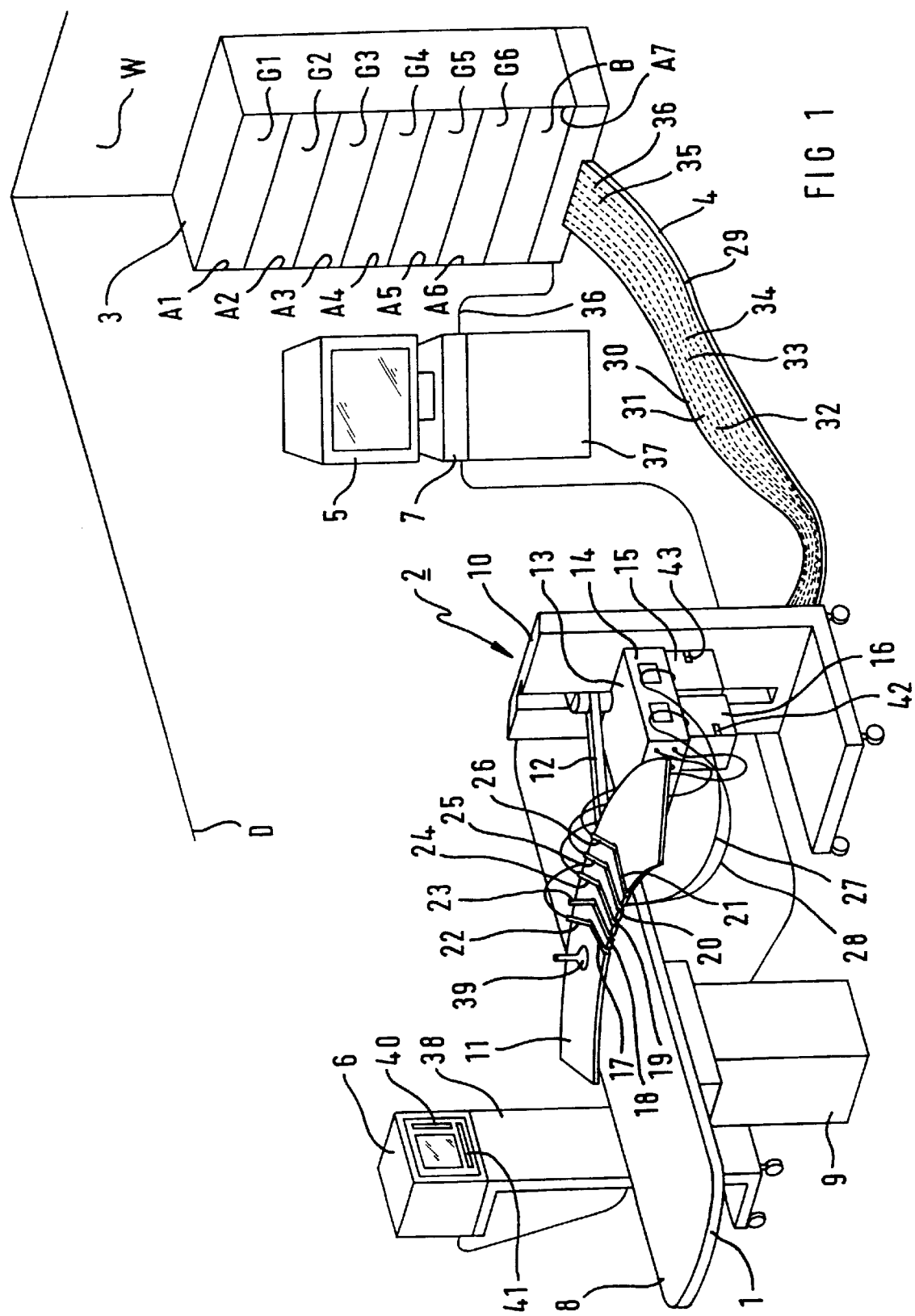
FIG. 1 shows an inventive medical system work station.

FIG. 1 shows an inventive medical system work station for open or minimally invasive surgery. The system work station includes a patient positioning table 1, a presenting unit 2, an equipment center in the form of an equipment cabinet 3, a connection unit 4 and a control computer 7, provided with monitors 5 and 6.

The patient positioning table 1 has a patient positioning plate 8 and a lifting column 9, so that the patient positioning plate 8 can be moved vertically in a known way.

The presenting unit 2, which includes among other things an equipment cart 10 that can be moved on wheels, is moved to the patient positioning table 1. A holder tray 11, of curved construction and oriented basically horizontally, is attached to the equipment cart 10, the tray 11 being connected with the equipment cart 10 via a height-adjustable, pivotable support arm 12. In addition, the presenting unit 2 has a terminal unit 13, attached to the equipment cart 10, for handheld (manipulated) instruments 22–26 of the medical devices. In addition, the equipment cart 10 is provided with a pump unit 14, arranged in the same housing as the terminal unit 13 in the present exemplary embodiment, and with containers 15 and 16 for rinsing (irrigating) and suction fluids.

The holder tray 11 is provided with receptacles 17–21 for the handheld instruments 22–26, in which the instruments 22–26 are held ready within the immediate reach of a surgeon working on the patient positioning table 1. In FIG. 1, the receptacles 17–21 are arranged in openings (not shown in more detail) in the holder tray 11, and can be removed from the holder tray 11. The openings, and the regions of the receptacles 17–21 that function with them, are constructed in such a way that different receptacles can be introduced into the same opening, i.e., receptacles for different instruments 22–26 can be exchanged for one another. The removability of the receptacles 17–21 proves to be advantageous for the sterilization thereof. By virtue of the mutually exchangeable receptacles 17–21, the holder tray 11 can be configured for different medical interventions with receptacles for the respectively required instruments, whereby, as already mentioned, the instruments are held ready in the corresponding receptacle provided therefor on the holder tray 11. The same receptacle can be suited for accepting different instruments.

The instruments 22–26 held ready by the holder tray 11 (in the present exemplary embodiment, an endoscopy camera with an integrated cold light 22, a rinsing/suction instrument 23, an ultrasound head 24, an insufflation instrument 25 and a bore instrument 26), are connected with their terminal lines to the terminal unit 13, via detachable couplings (not shown in more detail in FIG. 1). The endoscopy camera with integrated cold light 22 is thereby connected to an electrical terminal and to a light waveguide terminal, the rinsing/suction instrument 23 is connected with its hose lines 27, 28 to the pump unit 14, the ultrasound head 24 is connected to an electrical terminal, the insufflation instrument 25 is connected to a gas terminal, and the boring instrument 26 is connected to a compressed-air terminal. The endoscopy camera with integrated cold light 22 alternatively can be connected to only one terminal that includes both electrical contacts and contacts for light waveguides. The terminals of the terminal unit 13 thus can be constructed in such a way that one terminal has different types of contacts, e.g. electrical and optical contacts. The terminal unit 13 has a number of terminals of the same type and of different types, so that in practice all of the instruments of medical devices used in open or minimally invasive surgery can be connected to the terminal unit 13. The terminal unit 13 thus has more terminals than there are receptacles on the tray 11, so that the tray 11 can be configured arbitrarily with different instruments.

In addition, the terminal unit 13 and the support arm 12 represent the interface between the sterile part and the non-sterile part of the equipment cart 10. The support arm 12 can be removed from the equipment cart 10, and the holder tray 11 can be removed from the support arm 12, with both the support arm 12 and the holder tray 11 being constructed so that they can be autoclaved. The medical instruments 22–26 are likewise of sterilizeable construction with their terminal lines, and can be exchanged at any time. Thus, if the presenting unit 2 is prepared for a medical intervention, the holder tray 11, the support arm 12 and the instruments 22–26, with their terminal lines, have been previously sterilized.

The rinsing/suction instrument 23 is connected via the pump unit 14 to the container 15 with its hose line 27 for rinsing with a rinsing liquid, and is connected via the pump unit 14 to the container 16 with its second hose line 28 for the suctioning of body fluids. The pump unit 14 is connected electrically to the terminal unit 13. In this way, dependent on the mode of operation of the pump unit 14, during a surgical intervention it is possible with the rinsing/suction instrument 23 either to rinse the operational area or to suction body fluid, e.g. blood, from the operating area.

The equipment cart 10 is connected via the connection unit 4, which is constructed as a ribbon conductor 29, with the equipment cabinet 3, in which the non-manipulated components of the medical devices such as device control units belonging to the instruments 22–26 are arranged. The equipment cabinet 3 itself is arranged so as to be spatially separate from the equipment cart 10, but is placed at a minimum distance of 1.5 meters from the patient positioning table 1 or the terminal unit 13, e.g. on a wall W of the operating room. In this way, the devices are arranged at a point in the operating room that will not disturb the operation team, but it is possible for a single operator to monitor all the medical devices, and to operate them correspondingly in response to possible instructions, e.g. from the surgeon, or to provide information concerning the status of the devices. The equipment cabinet 3 need not necessarily be located in the operating room, but can be located outside the operating room if warranted.

In the present exemplary embodiment, the equipment cabinet 3 is provided with receptacles A1–A6 for an ultrasound device G1, a rinsing/suction pump control unit G2, a boring device control unit G3, an insufflator G4, a camera controller G5, a cold light device G6 and a receptacle A7 for an image memory B. In the present exemplary embodiment, the receptacles A1–A7 for the individual medical devices and control units G1–G6 and the image memory B are of essentially identical construction, and are respectively provided with a network terminal. The receptacle A4 for the insufflator G4 additionally has a terminal for a hose line connected with a carbon dioxide bottle. The network terminals and the carbon dioxide terminal of the insufflator G4 are not shown in FIG. 1.

As already mentioned, the equipment cabinet 3 is connected with the equipment cart 10 via the ribbon conductor 29, with both the equipment cabinet 3 and the equipment cart 10 having corresponding interfaces, not shown in more detail in FIG. 1, for the connection of the ribbon conductor 29. In the present exemplary embodiment, the ribbon conductor 29 contains, among other things, electrical connection cables 30, 31, 32, a light waveguide 33, a gas line 34 and a compressed-air line 35. In this way, e.g. the insufflation instrument 25 is connected with the insufflator G4 via the terminal unit 13 and the gas line 34, so that, according to corresponding controlling of the insufflator G4, carbon dioxide is supplied via the gas line 34 to the terminal unit 13, and from this unit to the insufflation instrument 25. Correspondingly, the ultrasound head 24 and the pump unit 14 are connected via the electrical connection cables 30, 31 to the ultrasound device G1 and to the suction/rinsing pump control unit G2, the endoscopy camera with integrated cold light 22 is connected via the electrical connection cable 32 and via the light waveguide 33 to the camera controller G5 and to the cold light device G6, and the boring instrument 26 is connected via the compressed-air line 35 to the boring device control unit G3.

The ribbon conductor 29, which, as mentioned, is connected via corresponding interfaces to the equipment cabinet 3 and to the equipment cart 10 (whose interface is connected to the terminal unit 13), is constructed so as to be deformable so that when the equipment cart 10 is moved relative to the equipment cabinet 3 the ribbon conductor 29 will follow after it. The internal wiring arrangement of the equipment cabinet 3 from the interface to the individual devices G1–G6 is not shown.

The medical devices or device control units G1 to G6 arranged in the equipment cabinet 3, and the image memory B, are connected to a common communication bus 36, but in FIG. 1 the individual connections of the communication bus 36 with the devices G1–G6 and with the image memory B are not shown. The communication bus 36 is connected with a control computer 7 arranged on a cabinet 37, which is operated via menu-controlled software in such a way that all the medical devices G1–G6 and the image memory B can be controlled from the control computer 7. The control computer 7 is thereby provided, in a way not shown in FIG. 1, with a keyboard and an operating device, e.g. a mouse or a keyboard or as shown in FIG. 1, a joystick 39. In this way, it is possible for a single operator to monitor all the medical devices from the control computer 7, which is provided with the monitor 5, and to operate them correspondingly upon instruction, e.g. from the surgeon. In addition, the second monitor 6, which in the present embodiment is placed on a cart 38, and is connected to the control computer 7, is arranged in the field of view of the operating surgeon. The images obtained by means of the endoscopy camera 22 in a known way are, for example, displayed on this monitor 6.

As noted, in the embodiment of FIG. 1, the holder tray 11 is provided with a central operating device in the form of a joystick 39, which is constructed so as to be protected by a temperature-resistant flexible plastic sheath in such a way that it can be autoclaved with the holder tray 11. The joystick 39 is likewise connected to the control computer 7 via the terminal unit 13 and the communication bus 36, which is routed via the ribbon conductor 29, the terminal unit 13 having corresponding terminals (not shown) for connecting the operating device to the communication bus 36. In this way, it is possible e.g. for an operating surgeon to control personally all the medical devices G1–G6 and the image memory B from the holder tray 11 as needed. The control computer 7 is operated with the already-mentioned menu-controlled software, and on the monitor 6, alongside the displayed images required for the operation, e.g. camera images from the endoscopy camera 22, a vertical menu bar 40 and horizontal menu bar 41 are shown. The surgeon can select individual menu points of the menu bars 40, 41 with a cursor that is mixed into the display screen of the monitor 6 by the control computer 7 and is allocated to the joystick 39, and can for example call status information from individual devices G1–G6, or give control instructions to the device control units G1–G6. For example, it is possible to control the suction/rinsing pump control unit G2 of the pump unit 14, arranged in the equipment cabinet 3, in such a way that the pump unit 14 pumps rinsing liquid from the container 15 through the hose line 27 and the instrument 23, or suctions body fluid into the container 16 via the instrument 23 and the hose line 28. Correspondingly, other devices can also be controlled via menu-controlled input.

In the present exemplary embodiment, the joystick 39 operates with a stepped switching, so that when the joystick 39 is actuated in a corresponding direction, i.e. an electrical signal is triggered, the cursor jumps to the next menu point in the direction of actuation. In addition, the joystick 39 has a triggering button (not shown in FIG. 1) whose actuation triggers the action allocated to a menu point. The joystick 39 need not necessarily operate with stepped switching, but can operate in a continuous manner, as is known.

In place of the joystick 39, or in addition to the joystick 39, other operating devices, e.g. foot switches, a receive unit for voice control, manually operated switches or other switching means can be provided that are connected to corresponding terminals of the terminal unit 13.

In the present embodiment, electrical sensors 42 and 43 for identifying the filling status are allocated to the containers 15 and 16, and are connected to the control computer 7 via the terminal unit 13 and the communication bus 36, so that the current filling status of the containers 15, 16 can be mixed into the image on the monitor 6 for the information of the surgeon. In this way, the surgeon is informed at all times of the filling status of the containers 15 and 16, and can have them exchanged at a given time.

In a way not shown in FIG. 1, the holder tray 11 can be constructed so as to be adjustable in a basically horizontal plane, i.e. the holder tray 11 can be moved in running fashion in a curved path on a rail (not shown). In addition, the holder tray 11 serves not only to hold medical instruments, but also mechanical medical instruments, e.g. clamps or conventional scalpels, which can be placed on the surfaces of the holder tray 11 that are available next to the joystick 39 and the receptacles 17–21.

Figure 2:
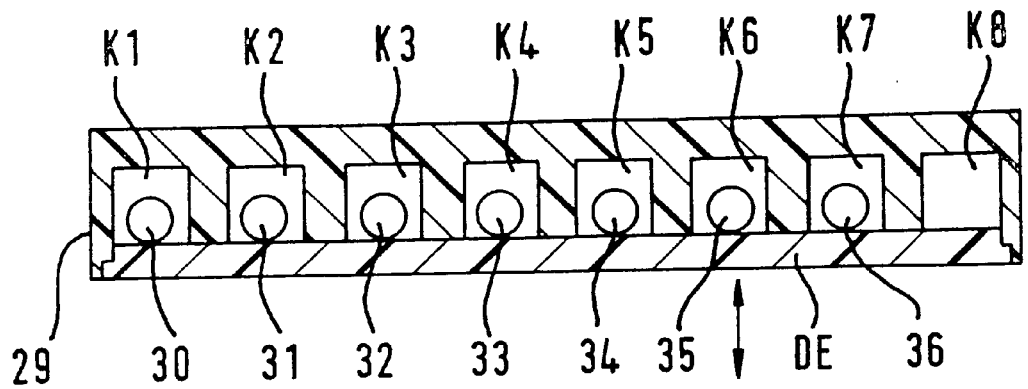
FIG. 2 shows the ribbon conductor from FIG. 1, in a schematic sectional view.

Corresponding to the modular construction of the equipment cabinet 3, the ribbon conductor 29 is constructed so that its electrical connection cables, light waveguides, gas lines and compressed-air lines can be added or removed. FIG. 2 schematically shows an example of the construction of the ribbon conductor 29. The ribbon conductor 29 has channels K1–K8, separated from one another by webs, with the electrical connection cables 30, 31, 32, the light waveguide 33, the gas line 34, the compressed-air line 35, and the communication bus 36 being guided in the channels K1–K7. The channel K8 is not occupied in the present embodiment. The ribbon conductor 29 is provided with a cover DE that seals the channels K1–K8. The cover DE can be removed from the ribbon conductor 29 (cf. double arrow in FIG. 2), so that, in a way not shown in more detail, electrical connection cables and/or light waveguides and/or gas lines and/or compressed air lines can be added to and removed from the ribbon conductor 29. The ribbon conductor can have fewer or more channels than the channels K1–K8 shown in FIG. 2.

In addition, the ribbon conductor 29 need not necessarily be connected with an interface of the equipment cart 10, but can be connected directly with a corresponding interface of the terminal unit 13.

Figure 3:
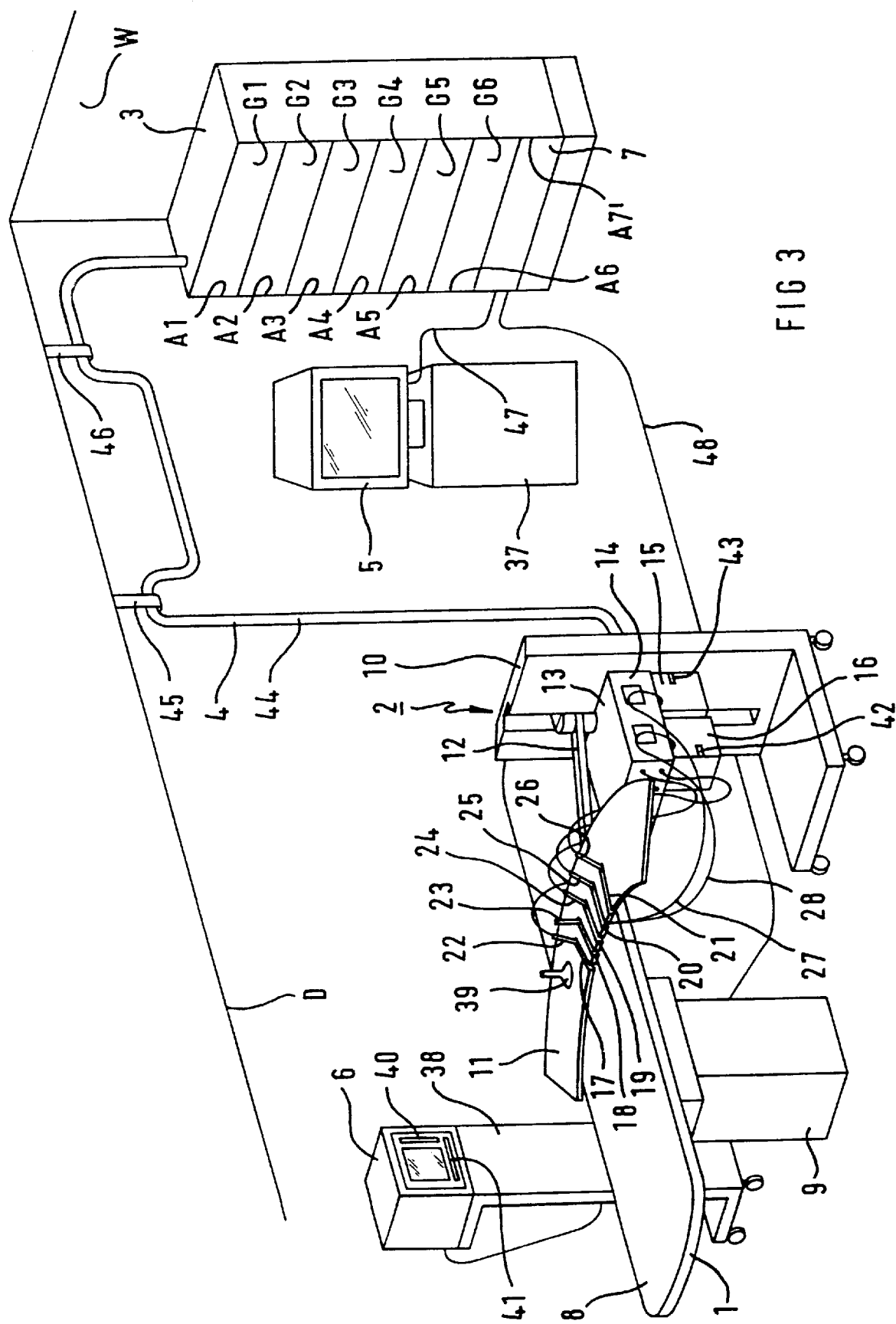
FIG. 3 shows a further embodiment of an inventive medical-technical system work station.

FIG. 3 shows a further embodiment of an inventive medical system work station, whereby components that are substantially identical to components of the system work station from FIG. 1 are provided with the same reference characters. The system work station shown in FIG. 3 differs from the system work station shown in FIG. 1 in that the terminal unit 13 of the equipment cart 10 is connected with the equipment cabinet 3 via a channeled tube 44.

Figure 4:
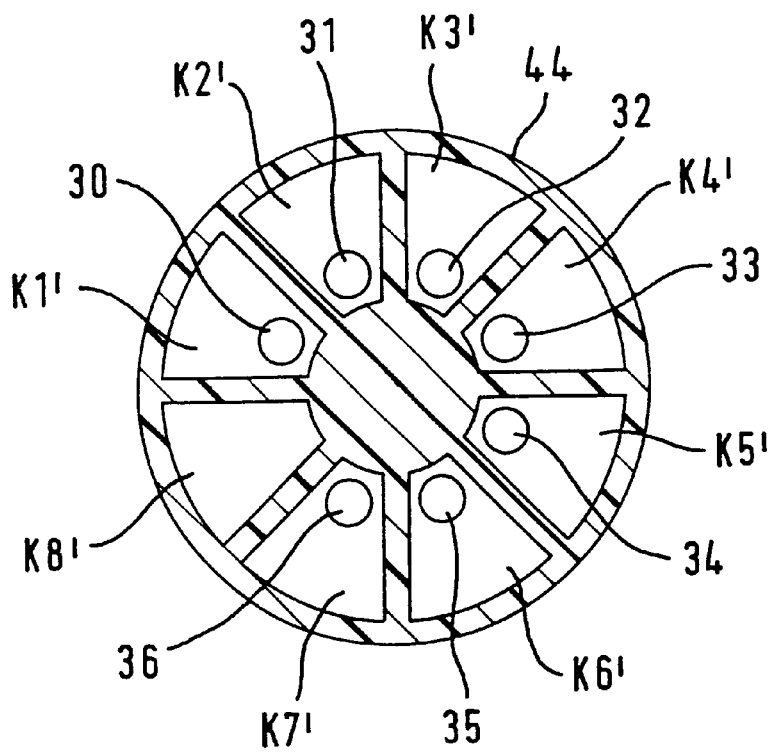
FIG. 4 shows the channeled tube from FIG. 3, in a schematic sectional view.

The channeled tube 44, shown schematically in FIG. 4, has channels K1'–K8', which, as in the ribbon conductor 29, are separated from one another by webs, whereby the electrical connection cables 30, 31, 32, the light waveguide 33, the gas line 34, the compressed-air line 35 and the communication bus 36 are guided in the channels K1'–K7'. The channel K8' is not occupied in the present embodiment. As in the ribbon conductor 29, electrical connection cables and/or light waveguides and/or gas lines and/or compressed air lines can be added to and removed from the channeled tube 44, in a way not shown in more detail. Lines that are no longer required are withdrawn from the channel of the channeled tube 44 that accepts them, or, respectively, new lines are pushed into a free chamber of the channeled tube 44. The channeled tube 44 can have fewer or more channels than the channels K1'–K8' shown in FIG. 4.

The channeled tube 44 is guided through channeled tube holders 45, 46 arranged on the ceiling D of the operating room, and has a length such that the equipment cart 10 with the channeled tube 44 connected to the terminal unit 13 can in practice be moved freely in the operating room. The channeled tube holders 45 and 46 can be moved in rails mounted on the ceiling D, in a way not shown, so that they can be brought into a position such that the channeled tube 44 runs vertically, approximately in a straight line, from the channeled tube holder 45 to the equipment cart 10. In this way, it is avoided that the channeled tube 44 runs transversely, in a disturbing manner, through the operating room. The terminal unit 13 and the equipment cabinet 3 have interfaces, not shown in FIG. 3, for connecting the channeled tube 44.

A further difference in the exemplary embodiment according to FIG. 3 in relation to the exemplary embodiment according to FIG. 1 is that the control computer 7 is integrated into the equipment cabinet 3. In this case, the control computer 7 is arranged in the receptacle A7. As in the embodiment described previously, the communication bus 36 connects, in a way not shown, the medical devices G1–G6, the filling state sensors 42, 43, the joystick 39 and the control computer 7 with one another. As in the embodiment described previously, the monitors 5 and 6 are connected to the control computer 7 via monitor cables 47 and 48.

Alternatively, the monitors 5 and 6 can be arranged, in a way not shown, on articulated arms mounted on the ceiling, wall, or floor, so that they can be positioned in the field of vision of e.g. the surgeon in the operating room.

The presenting unit 2 need not necessarily include the equipment cart 10. The presenting unit 2 can instead be a mounted holder, which is held by means of an articulated arm mounted on the ceiling, wall, or floor, and can be positioned in the operating room.

The holder tray 11 and the terminal unit 13 need not necessarily be arranged on the presenting unit 2. Rather, the holder tray 11 and the terminal unit can be arranged on separate mounts that can be moved independently of one another.

The embodiment of the equipment center as an equipment cabinet 3 is to be understood only as an example. The equipment cabinet 3 can be provided with more than the indicated receptacles for medical devices, e.g. with a laser, and with additional image memories. If all the medical devices cannot be integrated into one equipment cabinet, it is possible to add a second equipment cabinet, which is correspondingly connected with the terminal unit 13.

The inventive system work station can include several control computers and several connection units, and the presenting unit can include several terminal units.

The communication bus 36, routed in the ribbon conductor 29 or in the channeled tube 44, is considered as an electrical connection cable that can be removed from and added to the ribbon conductor 29 or the channeled tube 44.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system work station for invasive surgery, comprising:

a medical device comprising a handheld instrument and a non-manipulated component;

a holder tray for holding said instrument so as to be readily accessible for handheld use;

a terminal unit;

a first operating line connecting said terminal unit to said handheld instrument;

an equipment center, disposed remote from said terminal unit and retaining said non-manipulated component; and a connection unit connecting said terminal unit and said equipment center, said connection unit comprising a second operating line connecting said terminal unit and said non-manipulated component.

2. A medical system work station as claimed in claim 1 further comprising a presenting unit on which said holder tray and said terminal unit are mounted.

3. A medical system work station as claimed in claim 1 further comprising:

a control computer having a first control computer connection to said equipment center for operating said medical device; and a manipulable operating unit disposed on said holder tray and connected to said control computer via a second control computer line for operating said control computer.

4. A medical system work station as claimed in claim 3 wherein said non-manipulated component, said manipulable operating unit and said control computer are connected with each other via a communication bus.

5. A medical system work station as claimed in claim 3 wherein said equipment center contains said control computer.

6. A medical system work station as claimed in claim 1 wherein said equipment center comprises a receptacle for said non-manipulated component.

7. A medical system work station as claimed in claim 1 further comprising an image memory disposed at said equipment center.

8. A medical system work station as claimed in claim 1 wherein said connection unit comprises at least one second operating line selected from the group consisting of electrical connection cables, light waveguides, compressed air lines and gas lines.

9. A medical system work station as claimed in claim 1 wherein said connection unit comprises means for adding and removing additional second operating lines.

10. A medical system work station as claimed in claim 9 wherein said connection unit comprises a ribbon conductor, containing said second operating line, adapted to be laid on a floor.

11. A medical system work station as claimed in claim 9 wherein said connection unit comprises a channeled tube, containing said second operating line, adapted for mounting on a ceiling.

* * * * *

UNITED STATES PATENT AND TRADEMARK OFFICE
CERTIFICATE OF CORRECTION

PATENT NO.    : 6,117,127
DATED         : September 12, 2000
INVENTOR(S)   : Gerhard Helmreich et al.

It is certified that error appears in the above-identified patent and that said Letters Patent is hereby corrected as shown below:

<u>Claim 1, column 9,</u>
Line 19, before "a medical" insert -- plurality of --;
Line 19, delete "device" and substitute -- devices --;
Line 23, after "unit" insert -- comprising a plurality of terminals --;
Line 24, delete "a first operating line" and substitute -- a plurality of first operating lines respectively --;
Line 25, delete "instrument" and subtitute -- instruments --;
Line 27, delete "component" and substitute -- components --;
Line 28, delete "and";
Line 31, before "second operating" insert -- plurality of --, in the same line, delete "line" and substitute -- lines respectively --;
Line 32, delete "component" and substitute -- components --;
After line 32, insert the following:
a display
a control computer connected to said equipment center for operating said medical devices and connected to said display and operated via a menu-controlled software comprising a menu bar with individual selectable menu points displayed on said display, whereby each menu point is a-located to one of said medical devices to control said medical devices; and
a central operating device connected to said control computer for selecting one of said menu points.

Signed and Sealed this

Thirtieth Day of October, 2001

*Attest:*

NICHOLAS P. GODICI
*Attesting Officer*   *Acting Director of the United States Patent and Trademark Office*